(12) United States Patent
Bruder et al.

(10) Patent No.: US 8,306,303 B2
(45) Date of Patent: Nov. 6, 2012

(54) METHOD FOR IMPROVING THE QUALITY OF COMPUTED TOMOGRAPHY IMAGE SERIES BY IMAGE PROCESSING AND CT SYSTEM COMPRISING A COMPUTATIONAL UNIT

(75) Inventors: Herbert Bruder, Höchstadt (DE); Thomas Flohr, Uehlfeld (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 991 days.

(21) Appl. No.: 12/314,967

(22) Filed: Dec. 19, 2008

(65) Prior Publication Data

US 2009/0161935 A1 Jun. 25, 2009

(30) Foreign Application Priority Data

Dec. 21, 2007 (DE) .......................... 10 2007 061 935

(51) Int. Cl.
*A61B 6/03* (2006.01)

(52) U.S. Cl. ........................................................ 382/131

(58) Field of Classification Search ................. 378/4–20; 382/128–132
See application file for complete search history.

(56) References Cited

U.S. PATENT DOCUMENTS

| | | | |
|---|---|---|---|
| 2001/0014140 A1* | 8/2001 | Proksa et al. | 378/901 |
| 2006/0235293 A1 | 10/2006 | Raupach et al. | |
| 2007/0040831 A1 | 2/2007 | Flohr et al. | |
| 2007/0053605 A1 | 3/2007 | Ritter et al. | |
| 2007/0189635 A1* | 8/2007 | Borsdorf et al. | 382/275 |

FOREIGN PATENT DOCUMENTS

| | | |
|---|---|---|
| DE | 10305221 | 8/2004 |
| DE | 102005012654 A1 | 10/2006 |
| DE | 102005038892 | 3/2007 |
| DE | 102005038940 A1 | 3/2007 |
| DE | 102006005803 | 8/2007 |
| WO | WO 03/021530 | 3/2003 |

OTHER PUBLICATIONS

Wickborn, Examination of Siemens Patent Application 2007P19737DE SMA/LER, Nov. 2011, PTO 12-0917, Translation of German Office action of the same name, 12 pages.*

(Continued)

*Primary Examiner* — Toan Ton
*Assistant Examiner* — John Corbett
(74) *Attorney, Agent, or Firm* — Harness, Dickey & Pierce, P.L.C.

(57) ABSTRACT

A method, a computational unit and a CT system are disclosed for improving the quality of CT image series. In at least one embodiment, the method includes scanning an examination object over a period of time which permits the acquisition of at least two temporally offset projection data records of an identical recording region; generating at least two temporally offset tomographic image data records, each having a multiplicity of pixels, by reconstructing the projection data records; transforming the image data records into transformation data records of at least two spatial frequency ranges; calculating temporal fitted values of the transformation data records for some of the spatial frequency ranges, and replacing the values of the transformation data records which were fitted by the calculated fitted values; performing an inverse transform of the transformation data records with the fitted values to form new image data records; and displaying the new image data records.

27 Claims, 8 Drawing Sheets

OTHER PUBLICATIONS

Tischenko et al., An artefact-free, structure-saving noise reduction using the correction between two images for threshold determination in the wavelet domain, 2005, SPIE, vol. 5747, pp. 1066-1075.*

Montes et al., Noise Reduction by Temporal Estimation in Perfusion Computed Tomography, 2005, 2005 IEEE Nuclear Science Symposium Conference Record, pp. 2747-2751.*

Perona et al. "Scale-space and edge detection using anisotropic diffusion", IEEE Transactions on Pattern Analalysis and Machine Intelligence, vol. 12, pp. 629-639, 1990; Others.

J. Weickert, "Anisotropic Diffusion in Image Processing", Teubner-Verlag, Stuttgart, Germany, 1998; pp. 95-105.

"Enhanced Image Capture Through Fusion" by Peter J. Burt and Raymond J. Kolczynski in the Proc. Fourth International Conference on Computer Vision, 1993, pp. 173-182.

German Office Action dated Nov. 27, 2008.

* cited by examiner

I

II

III original    filtered

Difference: filtered minus original original    filtered

Difference: filtered minus original

METHOD FOR IMPROVING THE QUALITY OF COMPUTED TOMOGRAPHY IMAGE SERIES BY IMAGE PROCESSING AND CT SYSTEM COMPRISING A COMPUTATIONAL UNIT

PRIORITY STATEMENT

The present application hereby claims priority under 35 U.S.C. §119 on German patent application number DE 10 2007 061 935.0 filed Dec. 21, 2007, the entire contents of which is hereby incorporated herein by reference.

FIELD

Embodiments of the invention generally relate to a method for improving the quality of computed tomography image series by image processing. For example, embodiments may relate to a method wherein a multiplicity of temporally subsequent image data records are recorded and, if required, reconstructed by a CT system as an image series, and these image data records are improved by electronic filtering and postprocessing.

BACKGROUND

Methods for improving the quality of computed tomography image series by image processing are widely known. Reference is made in an example fashion to the document DE 10 2005 038 940 A1, in which an edge-maintaining filter is used to improve the image. The articles by P. Perona and J. Malik, Scale space and edge detection using anisotropic diffusion, IEEE Transactions on Pattern Analysis and Machine Intelligence, vol. 12, pp. 629-639, 1990; and J. Weichert, Anisotropic Diffusion Filtering in Image Processing, Teubner-Verlag, Stuttgart, Germany, 1998 use diffusion filters in order to improve the image quality. Reference is also made to the document DE 10 2005 012 654 A1, in which image data is filtered with the aid of correlation calculations so as to also improve the quality in this case.

However, all the abovementioned known methods for improving the quality of images by image processing reach their limits when the relevant contrast is in the region of or even smaller than the noise. If CT perfusion examinations of certain organs, such as brain, liver or heart, are considered, it can be shown that the typical changes in the CT value required for detecting the perfusion are in the range from approximately 2 to 20 HU, that is to say 0.2 to 2% of the contrast between water and air. Hence the pixel noise plays a decisive part.

SUMMARY

In at least one embodiment of the invention, a method is disclosed for improving the quality of computed tomography image series which makes significant noise-reduction possible. On the other hand, this measure should not simultaneously reduce the quality of the structure details in the image as well.

The inventors, in at least one embodiment, have recognized that in the case of relatively long examinations in which image series are recorded (e.g. perfusion examinations or cardio CT examinations), it is possible to obtain additional information from temporally adjacent images and this leads to a reduction of noise in the image, with the temporal resolution of such image series not necessarily being reduced due to clever application of this information. For this purpose, it is necessary to decompose the available image information with respect to its spatial frequencies since, for example, noise goes hand-in-hand with very high spatial frequencies, whereas temporal changes in the contrast in perfusion examinations only occur at low spatial frequencies. Contrast changes in the vessels themselves, for example, provide an exception to this; however, they are not relevant in the considered perfusion examinations, or they can be removed from consideration.

In accordance with this basic idea, in at least one embodiment the inventors propose a method for improving the quality of computed tomography image series which comprises:

scanning an examination object over a period of time which permits the acquisition of at least two temporally offset projection data records of an identical recording region, generating at least two temporally offset tomographic image data records, each having a multiplicity of pixels, by reconstructing the projection data records, transforming the image data records ($I_t$) into transformation data records of at least two spatial frequency ranges, calculating temporal fitted values of the transformation data records for some of the spatial frequency ranges, and replacing the values of the transformation data records which were fitted by the calculated fitted values, performing an inverse transform of the transformation data records with the fitted values to form new image data records, and displaying the new image data records.

Using this novel method of at least one embodiment illustrated above, it is now possible to consider the image information independently in accordance with its spatial frequency ranges and, depending on the requirements, carry out different measures with regard to improving this information.

By way of example, a wavelet transform is an advantageous option for transforming the image data records, in which the different spatial frequency ranges are reproduced by the different levels or planes of the wavelet transform. The wavelets can be used to determine the fitted values to be calculated.

A Fourier transform is another option for the transformation function. Here, the spatial frequency ranges are determined by Fourier coefficients assigned to a spatial frequency. Accordingly, the Fourier coefficients are used to determine the fitted values as well.

A third transformation option of the image data records will also be mentioned in an example manner; here, every spatial frequency range is filtered at least once using a spatial frequency filter from this spatial frequency range. The pixel values of the transformation data records are used to determine the fitted values.

As already explained above, the method according to at least one embodiment of the invention can be used, for example, to reduce the noise, wherein the temporal fitted values of the transformation data records are calculated for a spatial frequency range with relatively high spatial frequencies. Accordingly, the low-frequency spatial frequency ranges remain unconsidered or untreated in this application.

Another example option of the method according to at least one embodiment of the invention is to reduce artifacts in the image series of a gated CT examination. Such artifacts are largely generated due to the partial scans used for the higher resolution; that is to say only projections from a 180° range, and no redundant data, is used for the reduction. According to the invention, the temporal fitted values of the transformation data records from this type of examination are calculated for a spatial frequency range with low spatial frequencies, while the high spatial frequency ranges remain unconsidered or untreated.

Advantageously, temporally subsequent CT image data records from a similar movement phase can be used as an image series. That is to say a number of subsequent image data records are generated within one motion cycle, and they may overlap in time.

On the other hand, it is also possible that with respect to the movement phase, temporally subsequent CT image data records are used as the image series. That is to say, image series are generated which extend over a plurality of cycles and have an identical movement phase; that is to say the image data records of the image series originate from respectively the same point of time in the phase from subsequent motion cycles.

According to at least one embodiment of the invention, it is proposed to calculate temporal fitted values by forming averages over the entire image series. Alternatively, it is also possible to determine, and correspondingly use, a running average over the image series in order to calculate the temporal fitted values. In general, it is also possible to use weighted sums, wherein the weighting function can either have a flattening (e.g. trapezoidal functions) or a steepening characteristic (e.g. Laplace filter), or consist of a combination of the two.

The scope of at least one embodiment of the invention also includes a computational unit for image processing with program storage, in which this program storage comprises computer program code which executes the method steps of at least one embodiment of the method described above when the system is operational.

Additionally, an x-ray CT system with a control and computational unit with program storage is also within the scope of at least one embodiment of the invention, in which this program storage also comprises computer program code which executes the method steps of at least one embodiment of the method described above when the system is operational.

BRIEF DESCRIPTION OF THE DRAWINGS

In the following text, the invention will be explained in more detail with reference to the figures and on the basis of two example embodiments which relate to, on the one hand, noise reduction in low dosage CT images, in particular within the scope of a perfusion measurement, and, on the other hand, artifact reduction in cardio CT records. In the process, only those features required to understand the embodiments of the invention will be illustrated. The reference symbols and abbreviated references used are defined as follows: 1: CT system; 2: first x-ray tube; 3: first detector; 4: second x-ray tube; 5: second detector; 6: gantry housing; 7: patient; 8: displaceable patient couch; 9: system axis; 10: computational and control unit; 11: program storage; I: arterial blood vessels; II: normally perfused brain; III: cerebral matter with a reduced and, compared to II, delayed enhancement; σ: standard deviation; $a_{n,k}$: weighting vectors; CTA: computed tomography angiogram; $F^{(i)}$: weighting function; f: frequency; G: transform; $G^{-1}$: inverse transform; $I_t$: image data records of the time series; $\hat{I}_t^{(i)}$: image data records filtered according to spatial frequency ranges; $\tilde{I}_t$: new image data records of the time series; n: error propagation of the pixel values in the image processed according to the invention; NPS: noise power spectrum; o: error propagation of the pixel values in the original image; $Prg_1$ to $Prg_n$: computer programs.

In detail.

DETAILED DESCRIPTION OF THE EXAMPLE EMBODIMENTS

Figure 1:
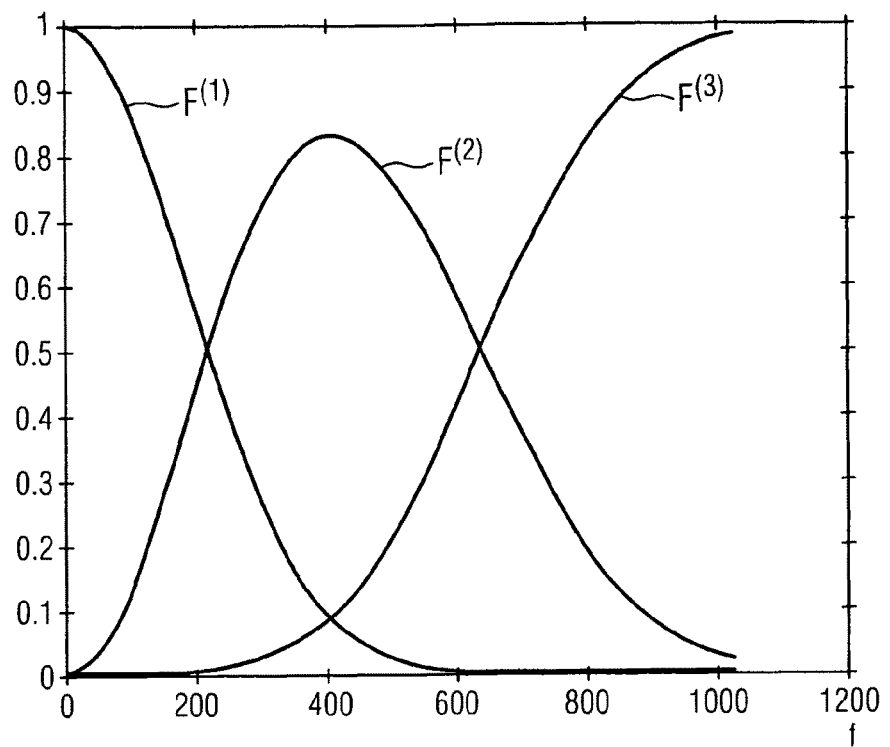
FIG. 1 shows simplified weighting functions for one frequency dimension and for N=3.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A—Noise Reduction

In a CT perfusion examination, the perfusion is determined using measurement values of the volume of blood, time to peak, etc. for a particular organ, e.g. the brain or liver. The functional information in many cases provides significantly more information than a CT angiography because it is not only possible to draw indirect conclusions about stenoses in the arteries, but the direct effects on the tissue are visible as well.

In order to be able to derive the corresponding variables from the tissue contrast (measured over time by the CT examination), a long scan—approximately 40 s—is carried out after the administration of contrast agents. However, such a long scan is connected to a relatively high organ dose. The radiation dose used in such examinations, such as CT perfusion measurements or dynamic CT angiography (CTA), is endeavored to be kept as low as possible. This is the only way that repeatedly undertaken examinations can be justified.

In these records, a time series of image data records with slice images or volume data is calculated from continuously recorded data. The tissue contrast as a function of time can then be determined by measuring the CT values. However, the typical change in the CT values only lies in the range of approximately 2-20 HU, that is to say only 0.2-2% of the contrast between water and air. Hence, pixel noise also plays a decisive part.

A reduction of the applied dose during the recording yields an increase in the noise of the image data, so that it is no longer possible to ensure that the CT values are determined with the required accuracy. Noise reduction using linear lowpass filters, e.g. using a very smooth convolution kernel, is simultaneously detrimental to the spatial resolution and hence the spatial definition of a particular area. In this case, the use of edge-maintaining image filters or diffusion filters, and filtering using correlation or other similar techniques reach their limits because the relevant contrast is of the order of the noise, or even smaller than the noise.

As already mentioned initially, the inventors have noticed that the change in the tissue contrast takes place in low spatial frequencies ranges, while the components of the data at high spatial frequencies only change slowly with time. The blood vessels themselves are an exception to this; however, their change in contrast is only used to determine the wash-in and can otherwise be excluded from the evaluation.

Hence, a relatively long scan is carried out to observe the perfusion profile in the tissue, with a temporal sequence of images or volume data, that is to say image data records $I_t$ in general, being made available from the scan's projection data post reconstruction. According to the invention, these can firstly be decomposed into N frequency bands, $\hat{I}_t^{(n)}$ (n=1,...,N), using a transform G such that the inverse transform $G^{-1}$ of these parts again results in the corresponding image itself, i.e.

$$I_t = G^{-1}\{\hat{I}_t^{(1)}, \ldots, \hat{I}_t^{(N)}\}. \quad (1)$$

Without loss of generality, $\hat{I}_t^{(1)}$ is the band with the lowest frequencies and $\hat{I}_t^{(N)}$ is the band with the highest frequencies. Different methods can be used for the transform, such as a:
1) wavelet transform, with $\hat{I}_t^{(n)}$ referring to the coefficients in the n-th level;
2) Fourier transform combined with frequency dependent weighting functions $F^{(n)}$ such that their sum is normalized, i.e $$\sum_{n=1}^{N} F^{(n)} \equiv 1, \text{ and } \hat{I}_t^{(n)} = F^{(n)}(G\{I_k\});$$

or a
3) filtering with filters $F^{(n)}$ for different frequencies or frequency bands 1,...,n which have the property that $$\sum_{n=1}^{N} F^{(n)}(I_t) = I_t$$

holds.

FIG. 1 sketches possible simplified weighting functions/frequency filters $F^{(i)}$ for N=3 in a single frequency dimension.

Thus, the ordinate shows a dimensionless weighting or transfer factor, while the abscissa shows the frequencies in arbitrary units.

Since thick layers, and not isotropic volume data, are generally used for CT perfusion examinations, the transform G can advantageously be applied in a two-dimensional fashion; namely in the plane perpendicular to the rotational axis of the gantry. However, a three-dimensional decomposition of volume data, in particular for the application to dynamic CTAs, is also possible.

New image data records $\tilde{I}_t$ can be calculated as follows from the components in the respective frequency bands at the different times:

$$\tilde{I}_t = G^{-1}\left\{\sum_k a_{1,k} \hat{I}^{(1)}_{t+k}, \ldots, \sum_k a_{N,k} \hat{I}^{(N)}_{t+k}\right\}. \quad (2)$$

The weightings $a_{n,k}$ have to be normalized for each band, that is to say $$\sum_k a_{n,k} = 1 \text{ for all } n, \quad (3)$$

and must have a vanishing first moment, that is to say $$\sum_k k \cdot a_{n,k} = 0 \text{ for all } n. \quad (4)$$

The temporal focus of the images calculated in accordance with (2) is retained due to the abovementioned conditions. The coefficients are preferably symmetric in time, i.e.

$$a_{n,k} = a_{n,-k}, \quad (5)$$

so that condition (4) is satisfied automatically. As a result of the weighted average over a plurality of times in certain bands in accordance with (2), the image data record of the resultant image $\tilde{I}_t$, which has undergone an inverse transform, has less noise than the image data record of the original image $I_t$.

Figure 2:
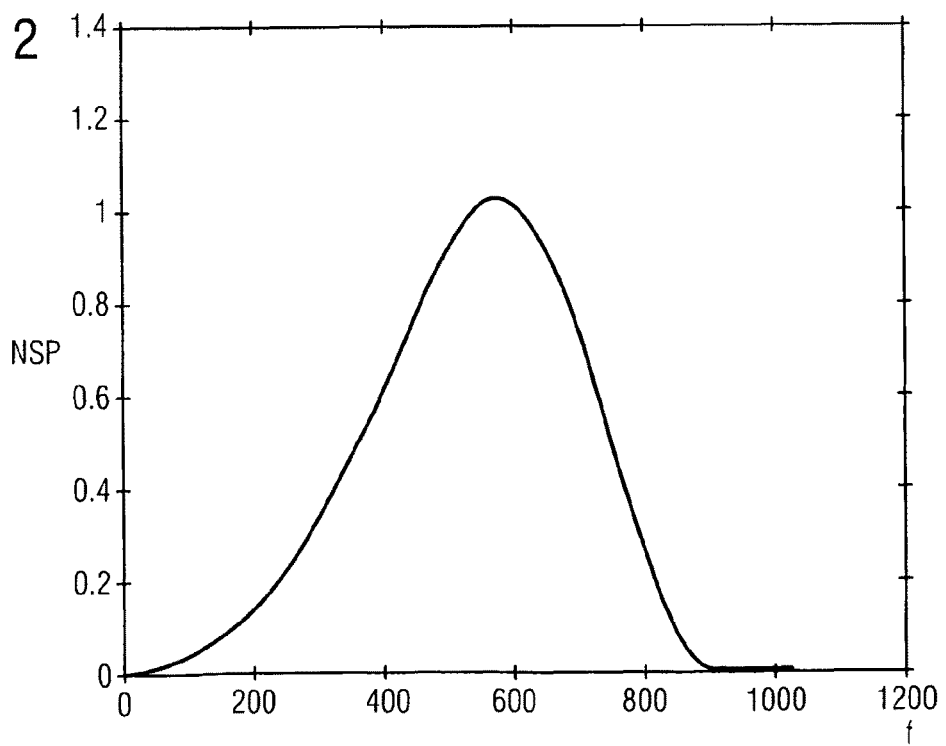
FIG. 2 shows a typical (radial) noise power spectrum for a CT image.

Qualitatively, $a_{1,k}$ should have a "narrow" form, i.e. $a_{1,0}=1$ and $a_{1,k}=0$ for $k \neq 0$. This ensures that the temporal sensitivity profile is not made worse at low frequencies, and corresponds to that of the original data; this is within the meaning of the findings mentioned initially. Furthermore, only a small amount of noise can be removed from low frequencies since the CT noise power spectrum there only has low amplitude. This can be seen in the diagram illustrated in FIG. 2, which shows a typical radial noise power spectrum for a CT image.

Figure 3:
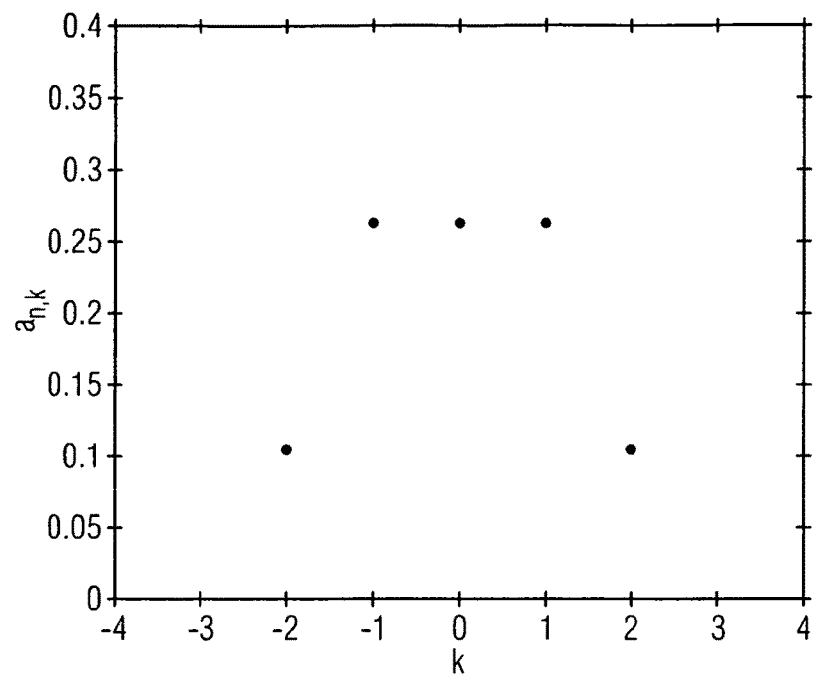
FIG. 3 shows an illustration of the weighting coefficients.

The band $a_{N,k}$ should have the largest temporal width so that the temporal sensitivity profile is only significantly widened at the highest frequencies. By way of example, the coefficients k can have a trapezoidal shape, as shown in FIG. 3.

Overall, compared to the original image $I_t$, the resultant image $\tilde{I}_t$ thus has a frequency dependent temporal sensitivity profile and reduced noise.

In order to optimize the noise reduction, the band which contains those frequencies which, according to the noise power spectrum, most strongly contribute to the pixel noise is particularly relevant.

Figure 4:
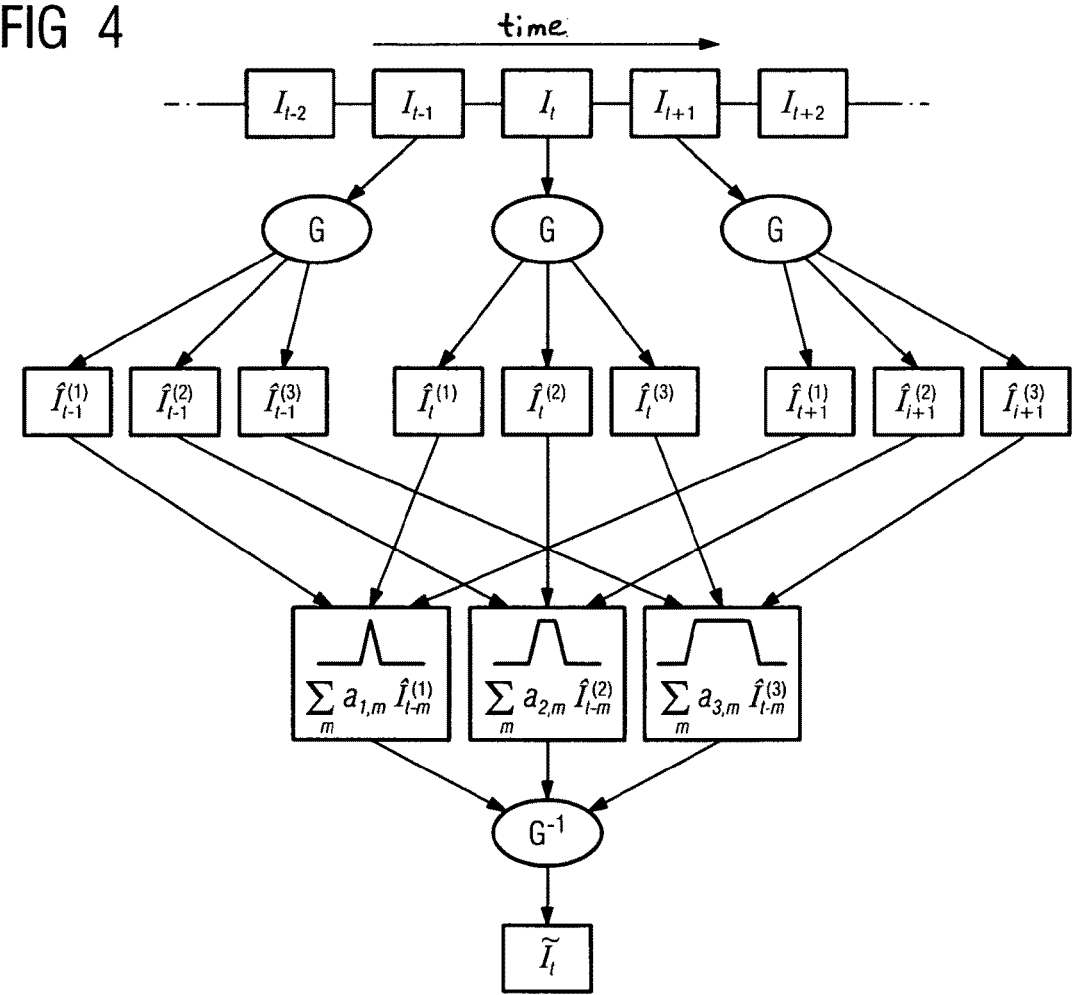
FIG. 4 shows a schematic illustration of the data flow for N=3.
Figure 5:
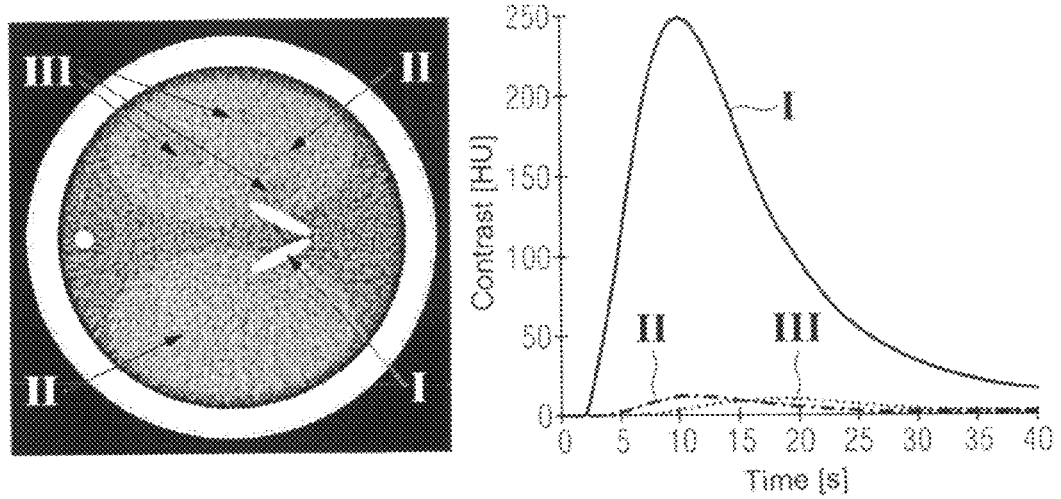
FIG. 5 shows a simulated phantom (left) with a temporal contrast profile (right)

The scheme illustrated in FIG. 4 shows a flowchart for the overall data flow in the case where N=3 and a maximum temporal length of the weighting vectors $a_{n,k}$ is three sampling points.

In order to demonstrate the method described above, a skull-like phantom with a time-dependent contrast was simulated, and the results thereof are illustrated in FIGS. 5 to 8. In the left image of the phantom in FIG. 5, the arterial blood vessels are referred to by I, normally perfused brain by II and cerebral matter with a changed perfusion, that is to say with a reduced enhancement and a longer time-to-peak duration, is referred to by III. A gantry rotation time of 1 s was assumed during the simulation, and output images $I_t$ were reconstructed at an interval of 1 s with the temporal foci at t=0.5 s, 1.5 s, 2.5 s, . . . . The temporal contrast profile of the phantom illustration illustrated on the left is shown in the diagram next to it on the right. The contrast profiles of the individual tissue types I, II and III are illustrated therein as HU values over time t.

Figure 6:
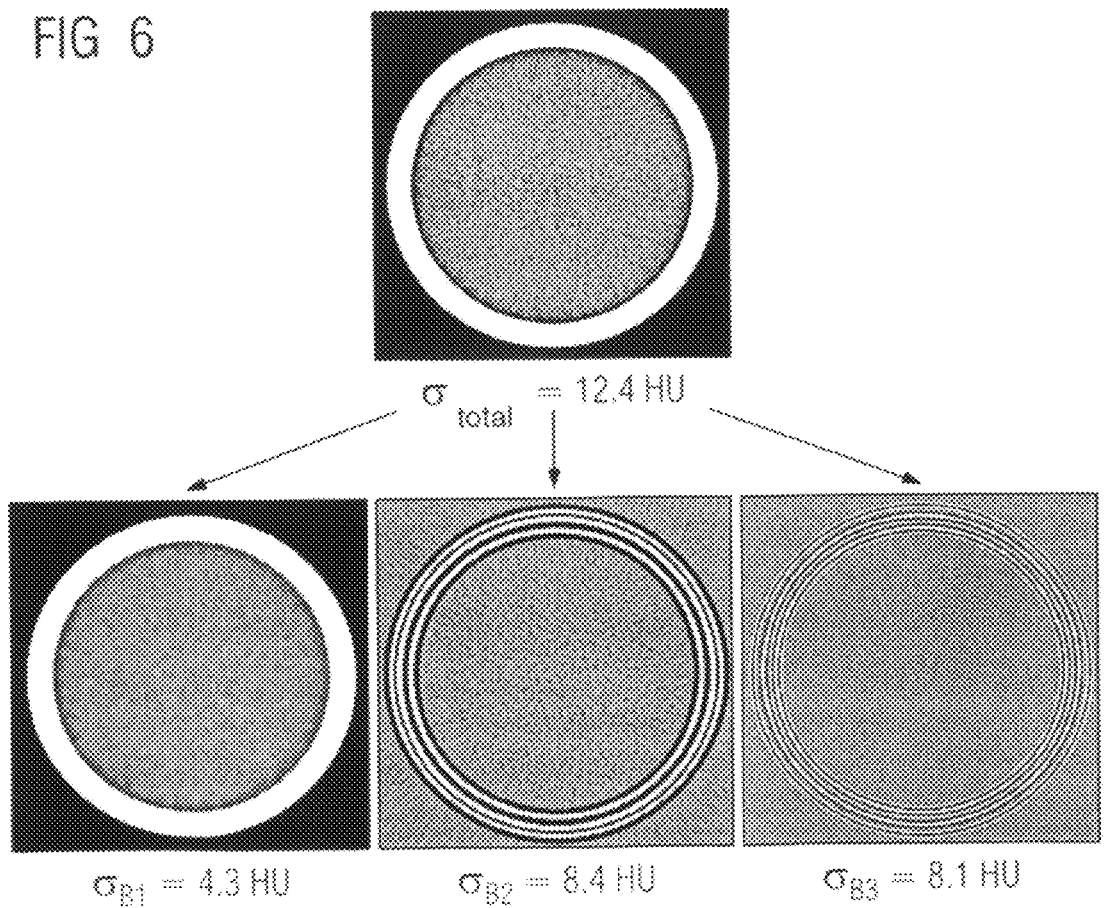
FIG. 6 shows the decomposition of output images into three frequency bands by means of a Fourier transform.

FIG. 6 shows, in an example manner, the decomposition of a section of an output image (top) into three spatial frequency bands at t=0.5 s. A Fourier transform and three frequency bands, which were generated by isotropic filters with radial cuts in the frequency representation in accordance with FIG. 1, were used as the transform in this example. The noise power is mainly concentrated in the two upper bands. The weighting was selected as follows:

$a_{1,k}=[0\ 0\ 0\ 1\ 0\ 0\ 0]$, $a_{2,k}=[0\ 1\ 3\ 4\ 3\ 1\ 0]/12$, $a_{3,k}=[1\ 3\ 4\ 4\ 4\ 3\ 1]/20.$ \quad (6)

Figure 7:
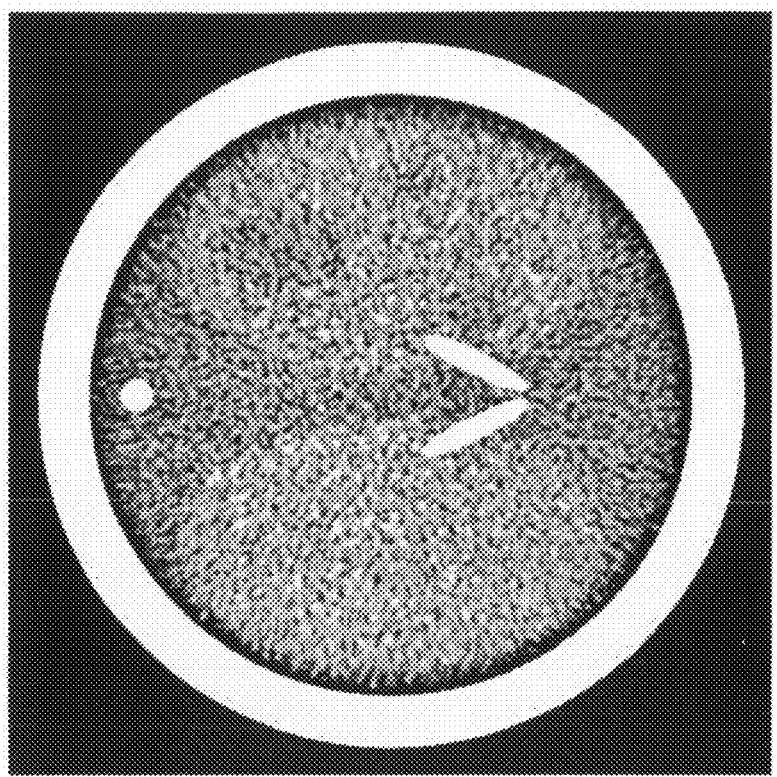
FIG. 7 shows the effect of the method according to an embodiment of the invention on an individual image, displayed before and after application of the method.
Figure 7:
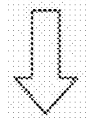
Figure 7:
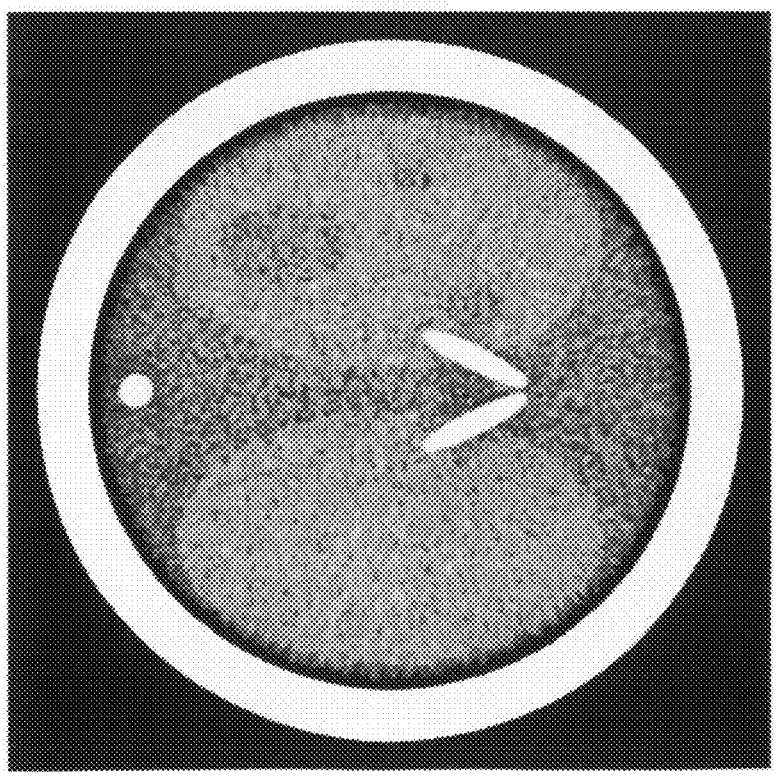

By applying the method using these parameters, the noise in the individual image is reduced by a factor of approximately 2.4. A comparison between the original image, top, and the image with the noise reduction according to an embodiment of the invention, bottom, at time t=7.5 s is shown in FIG. 7.

When measuring a contrast-time curve in individual pixels, the deviation from the exact curve, measured in a simulation without noise, is significantly reduced.

Figure 8:
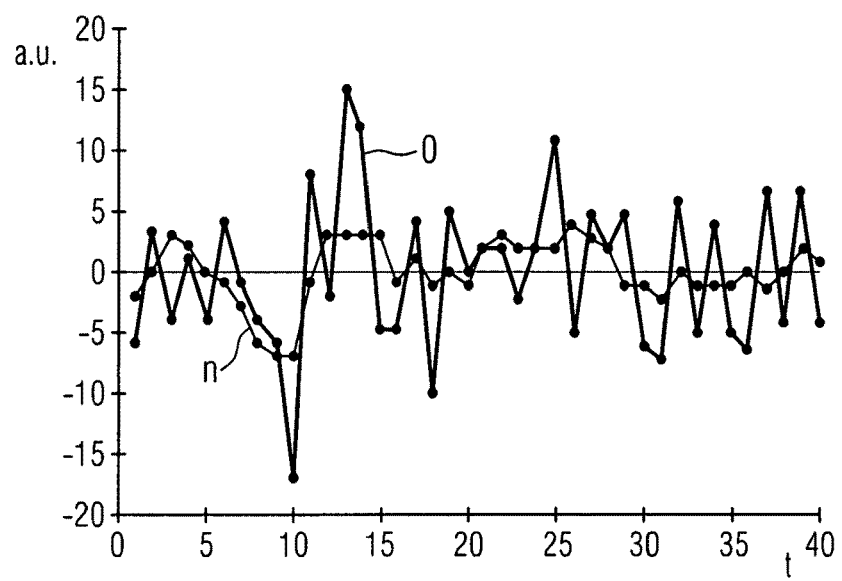
FIG. 8 shows the errors of the pixel values over time in three tissue regions I, II and III.
Figure 8:
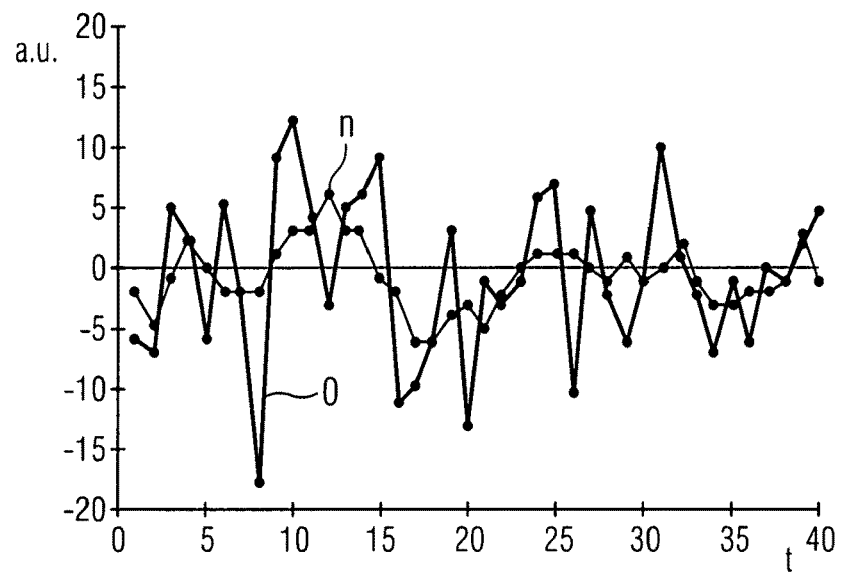
Figure 8:
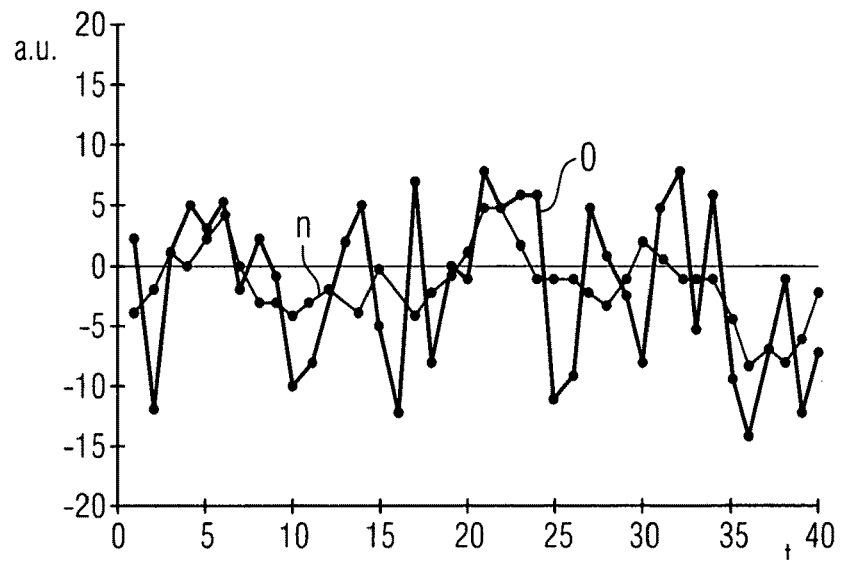

Finally, FIG. 8 shows the error of pixel values in HU over time in the three typical tissue types I, II and III, with the "o" curves respectively originating from the corresponding regions of the original image without applying the method according to the invention, and the "n" curves respectively originating from the corresponding regions of the image by applying the method according to an embodiment of the invention. Using an embodiment of the invention, the standard deviation of the errors reduces from 6.5 HU to 2.6 HU in tissue type I, that is to say by a factor of 2.5; from 6.8 HU to 2.7 HU in tissue type II, that is to say by a factor of 2.5; and from 6.7 HU to 3.0 HU in tissue type III, that is to say by a factor of 2.2.

Reference is also made to the fact that the determined time-contrast curves of the images after applying the method according to an embodiment of the invention cannot by generated by filtering the time-contrast curves of the output images.

B—Artifact Reduction in Cardio CT

Gated reconstructions are used in x-ray computed tomography (CT) when a moving organ is intended to be imaged in a defined movement state. This relates in particular to imaging the heart and lungs. These applications generally also require a high temporal resolution, so the shortest-possible data segment is used for the image reconstruction. This means that when reconstructions with a parallel geometry are used, data segments from a rotation of radiation source through 180 degrees plus the total aperture angle of the fan are used. Although such partial rotation scans have an optimal temporal resolution, they are susceptible to artifacts, particularly at low spatial frequencies, because complementary beams are not used. As a result of this, quantitative statements using CT values which require a high precision are problematic. For example, this includes perfusion measurement of the myocardium and dual-energy applications in the region of the heart and lung. In this case, the method according to an embodiment of the invention for improving the quantitative image properties can also be used while simultaneously maintaining a high temporal resolution.

Until now, the typical artifacts in partial rotation scans described above could not be avoided unless a complete rotation was used for the reconstruction instead of a partial rotation. However, this would mean a return to square one, because in this case the temporal resolution again corresponds to that of a complete rotation, with all its advantages and disadvantages. However, applying the method according to an embodiment of the invention in the case of a gated CT represents an ideal compromise, since the data from a complete rotation, or from even more than one complete rotation, is used exclusively for noise reduction, while the reconstruction itself is based on the data from a partial rotation and has a correspondingly high temporal resolution.

The modifications used, which differ from the method described previously in part A, are described below in an example manner and without loss of generality by way of a cardiac reconstruction using EKG gating.

Figure 9:
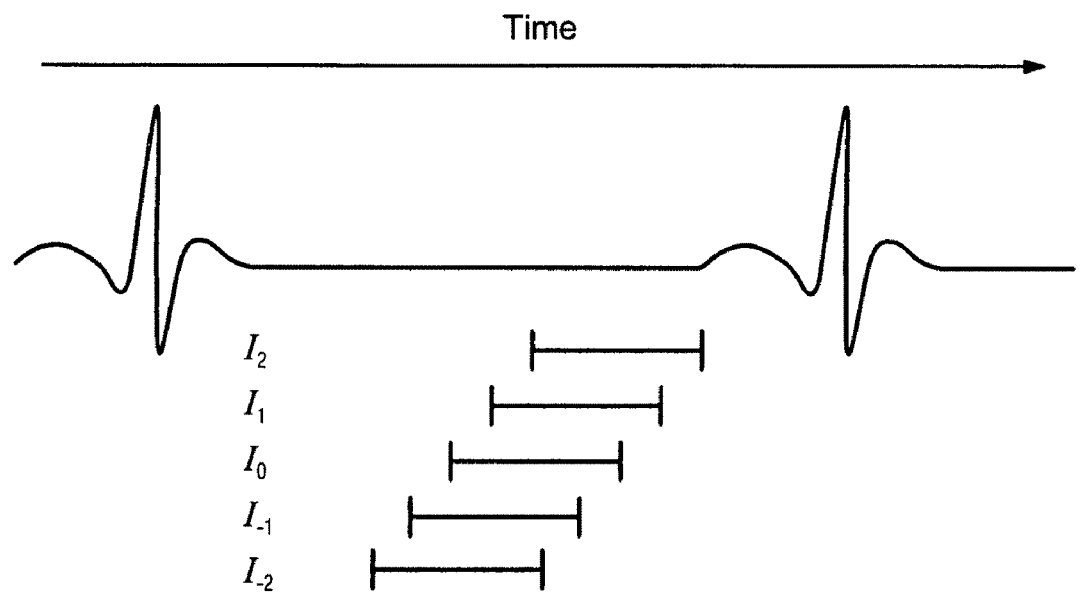
FIG. 9 shows a schematic illustration of the temporal correlation of the image data to the movement phase relative to an EKG profile.

1) The image reconstruction of volume data or respectively part of the volume data is carried out using raw data from the appropriate phase of one or more cardiac cycles. Correspondingly, in the case of lung data being reconstructed, this is carried out using raw data from the appropriate phase of one or more respiratory cycles. In order to apply the proposed method, a times series of the corresponding partial volume or volume is firstly reconstructed in such a manner that the temporal scan has sufficient quality, e.g. a half of a temporal sensitivity profile to satisfy the sampling theorem. The timing, in particular the temporal cover of individual slice images $I_t$ over the cardiac phase (illustrated by way of an EKG profile), is sketched in an exemplary manner in FIG. 9. The individual data segments are selected to be as short as possible with the goal of an optimum temporal resolution.

The (partial) volume $I_0$ in this case represents the actually required phase or the actually required reconstruction time. Advantageously, the union of the raw data used for the reconstruction of the image data $I_n$ covers a complete rotation.

Figure 10:
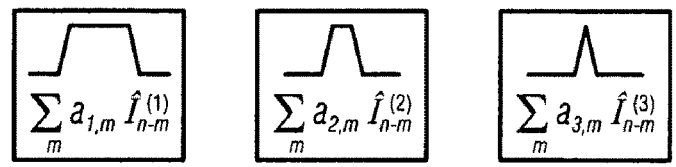
FIG. 10 shows a symbolic illustration of the filter functions for three frequency bands.

2) A filtered (partial) volume $\tilde{I}_0$ is calculated from the input images in accordance with the method described above in part A, in which the filter functions in the temporal direction however are selected deviating from this method in such a manner that the filter in the highest frequency band is very narrow, and the widest filter is used for the lowest frequency band. FIG. 10 shows three example filters.

As a result of this, the highly resolved spatial information is still available at high temporal resolution, whereas the low frequency partial rotation artifacts are reduced.

3) The method can be applied to other cardiac cycles in an analogous manner so as to reconstruct the remaining partial volumes.

For the purposes of demonstrating the method, a clinical data record of a coronary cardiac CTA examination by a "SOMATOM Definition" CT system is shown in an example fashion. First of all, slice images $I_n$ (n=−3, . . . , 3) with a temporal resolution of 82 ms and a temporal increment of in each case 20 ms were reconstructed, with the image data $I_0$ reproducing the optimum end systolic or end diastolic rest phase.

Figure 11:
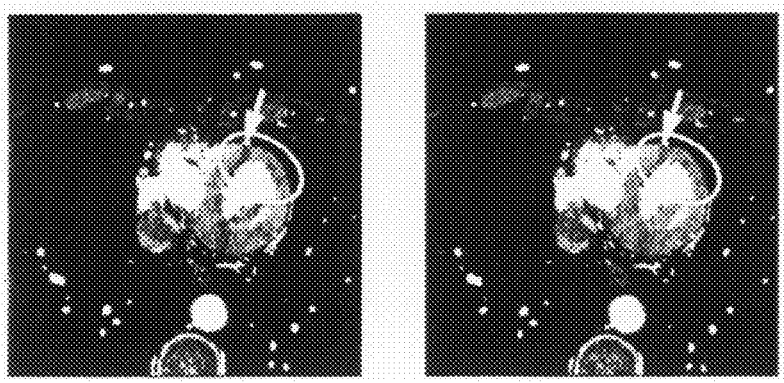
FIG. 11 shows images of a coronary CTA with the original image/output image (top left), an image treated according to an embodiment of the invention (top right) and a difference image (bottom) of the two.
Figure 11:
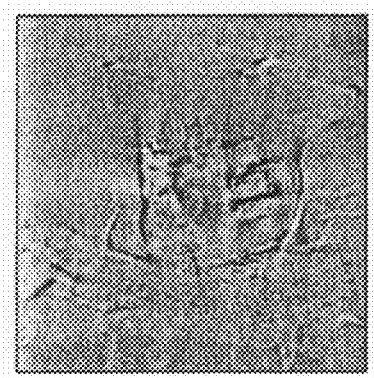
Figure 12:
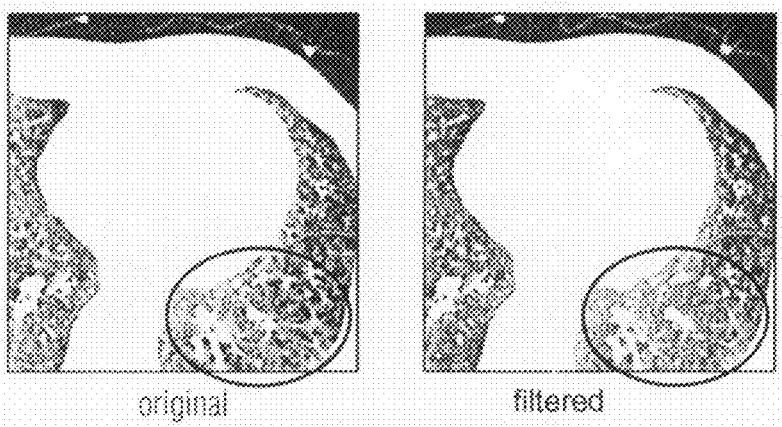
FIG. 12 shows images of a lung CT record with the original image/output image (top left), an image treated according to an embodiment of the invention (top right) and a difference image (bottom) of the two.
Figure 12:
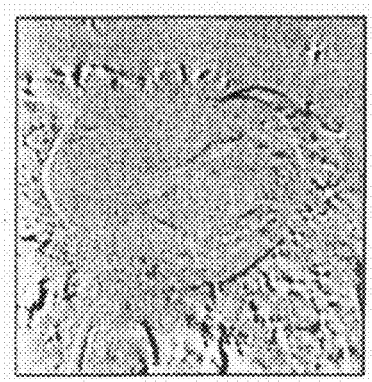

In accordance with the notation from part A, the filter functions $a_{1,k}$=[1 3 4 4 4 3 1 1]/20, $a_{2,k}$=[0 1 3 4 3 1 0 1]/12, $a_{3,k}$=[0 0 0 1 0 0 0], (7)

which comprise the characteristics demanded by (1) to (5), were selected. FIGS. 11 and 12 in each case show individual slice images before and after filtering using the method according to an embodiment of the invention, and they also show a difference image.

FIG. 11 shows—top left—an original image, without the image being treated according to an embodiment of the invention, and—top right—the image, filtered and processed according to the invention, of a cardiac record, while a difference image (filtered minus original) is illustrated below. Correspondingly, FIG. 12 shows—top left—an original image, without the image being treated according to the invention, and—top right—the image, filtered and processed according to the invention, of a record of the lungs, while a difference image—filtered minus original—is illustrated below.

A significant improvement of the homogeneity of the myocardium and the lung parenchyma can be seen while the vessels remain illustrated in focus, that is to say without movement artifacts.

Figure 13:
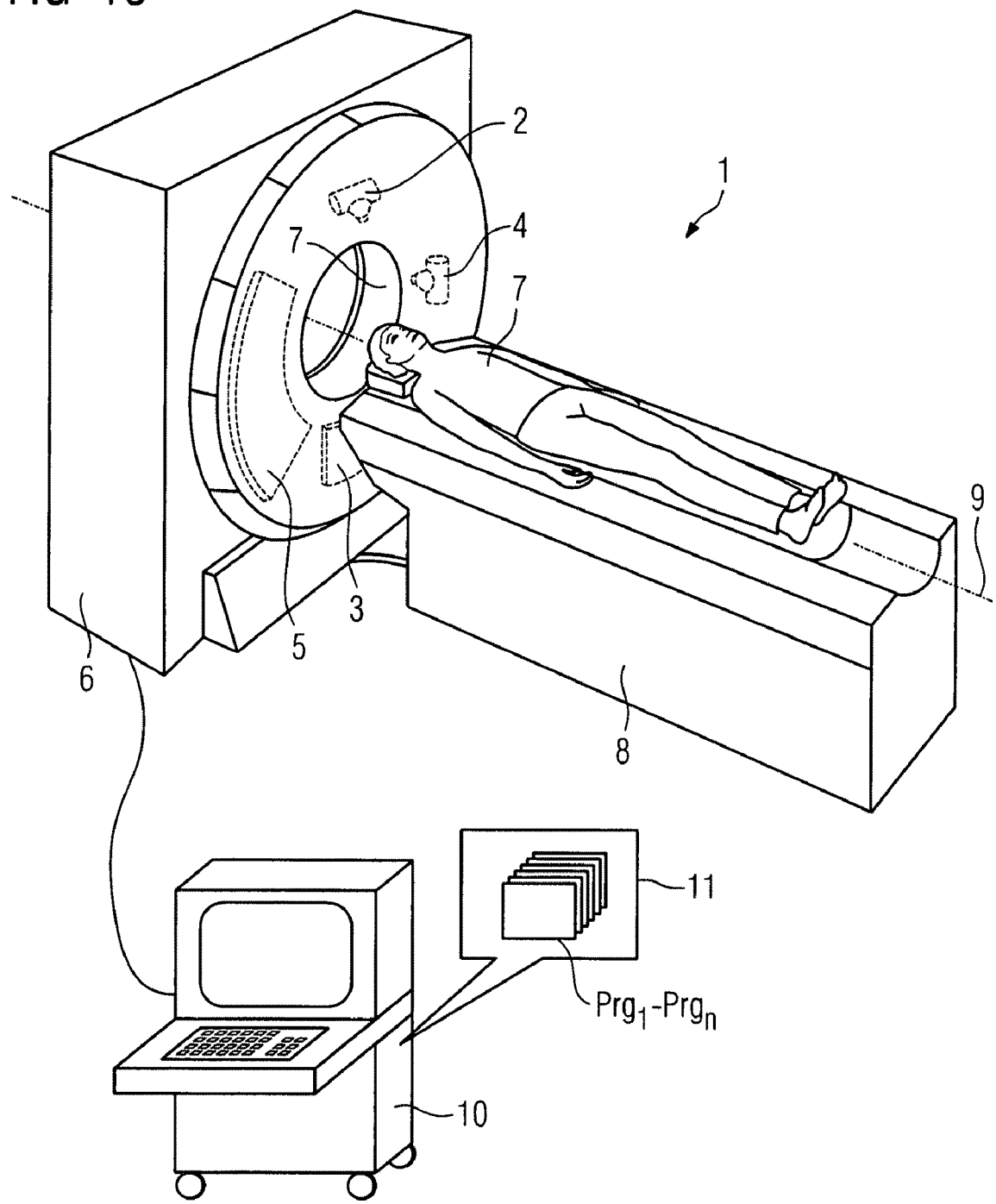
FIG. 13 shows a CT system for carrying out the method according to an embodiment of the invention.

FIG. 13 illustrates, in an example manner, a CT system 1 which is suitable for carrying out the method according to an embodiment of the invention. This CT system comprises a gantry housing 6, with a first beam/detector system, comprising a first x-ray tube 2 and a first detector 3 lying opposite thereof, being arranged on the gantry which is not illustrated in any more detail. Optionally, further emitter/detector systems can be provided, like the second emitter/detector system, with a second x-ray tube 4 and a second detector 5 lying opposite thereof, shown here in an example manner. The patient 7 is located on a displaceable patient couch 8 so that, during the CT examination, he can be pushed along the system axis 9 and through the measurement field of the CT system 1 in a continual or sequential manner. Likewise, a forward and backward motion can be carried out during the examination so that a zigzag spiral can be driven. By way of example, the method according to an embodiment of the invention can run on the control and computational unit 10, with computer programs $Prg_1$ to $Prg_n$, which are saved in the schematically illustrated storage 11, being able to, inter alia, execute the method according to an embodiment of the invention when run.

It is understood that the abovementioned features of embodiments of the invention can be used not only in the respectively specified combination, but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for improving the quality of computed tomography image series, comprising:
   scanning an examination object over a period of time which permits an acquisition of at least two temporally offset projection data records of an identical recording region;
   generating at least two temporally offset tomographic image data records, each including a multiplicity of pixels, by reconstructing the projection data records;
   transforming the image data records into transformation data records of at least two spatial frequency ranges;
   calculating temporal fitted values of the transformation data records for some of the spatial frequency ranges, and replacing the values of the transformation data records fitted by the calculated fitted values;
   performing an inverse transform of the transformation data records with the fitted values to form new image data records; and
   displaying the new image data records.

2. The method as claimed in claim 1, wherein a wavelet transform is used to transform the image data records.

3. The method as claimed in claim 2, wherein the spatial frequency ranges are determined by a plane of the wavelet transform.

4. The method as claimed in claim 3, wherein the wavelets are used to determine the fitted values.

5. The method as claimed in claim 2, wherein for noise reduction, the temporal fitted values of the transformation data records are calculated for a spatial frequency range with relatively high spatial frequencies.

6. The method as claimed in claim 2, wherein, in order to reduce artifacts in image series in a gated CT examination of a cyclically moving or moved organ of a patient, the temporal fitted values of the transformation data records are calculated for a spatial frequency range with relatively low spatial frequencies.

7. The method as claimed in claim 2, wherein averages are determined over the entire image series and are used to calculate temporal fitted values.

8. The method as claimed in claim 2, wherein running averages are determined over the image series and are used to calculate temporal fitted values.

9. The method as claimed in claim 2, wherein weighted sums are determined and are used to calculate temporal fitted values.

10. A computational unit for image processing comprising:
    a non-transitory computer readable medium configured to store computer program code which executes the method of claim 2 when the computational unit is operational.

11. An x-ray CT system comprising:
    a control and computational unit including a non-transitory computer readable medium configured to store computer program code which executes the method of claim 2 when the system is operational.

12. A non-transitory computer readable medium including program segments for, when executed on a computer device, causing the computer device to implement the method of claim 2.

13. The method as claimed in claim 1, wherein a Fourier transform is used to transform the image data records.

14. The method as claimed in claim 13, wherein the spatial frequency ranges are determined by the Fourier coefficients assigned to a spatial frequency.

15. The method as claimed in claim 14, wherein the Fourier coefficients are used to determine the fitted values.

16. The method as claimed in claim 1, wherein, in order to transform the image data records, each spatial frequency range is filtered at least once using a spatial frequency filter from the spatial frequency range.

17. The method as claimed in claim 16, wherein the pixel values of the transformation data records are used to determine the fitted values.

18. The method as claimed in claim 1, wherein for noise reduction, the temporal fitted values of the transformation data records are calculated for a spatial frequency range with relatively high spatial frequencies.

19. The method as claimed in claim 1, wherein, in order to reduce artifacts in image series in a gated CT examination of a cyclically moving or moved organ of a patient, the temporal fitted values of the transformation data records are calculated for a spatial frequency range with relatively low spatial frequencies.

20. The method as claimed in the preceding patent claim 19, characterized in that temporally subsequent CT image data records from the same movement phase are used as the image series (It+1, It, It−1).

21. The method as claimed in claim 19, wherein, with respect to the movement phase, temporally subsequent CT image data records are used as the image series.

22. The method as claimed in claim 1, wherein averages are determined over the entire image series and are used to calculate temporal fitted values.

23. The method as claimed in claim 1, wherein running averages are determined over the image series and are used to calculate temporal fitted values.

24. The method as claimed in claim 1, wherein weighted sums are determined and are used to calculate temporal fitted values.

25. A computational unit for image processing comprising:
a non-transitory computer readable medium configured to store computer program code which executes the method of claim 1 when the computational unit is operational.

26. An x-ray CT system comprising:
a control and computational unit including a non-transitory computer readable medium configured to store computer program code which executes the method of claim 1 when the system is operational.

27. A non-transitory computer readable medium including program segments for, when executed on a computer device, causing the computer device to implement the method of claim 1.

* * * * *